United States Patent [19]

Kita et al.

[11] Patent Number: 4,840,869
[45] Date of Patent: Jun. 20, 1989

[54] LIGHT-SENSITIVE COMPOSITION

[75] Inventors: Noriyasu Kita, Musashimurayama; Kiyoshi Goto, Hachioji, both of Japan

[73] Assignee: Konishiroku Photo Industry Co., Ltd., Tokyo, Japan

[21] Appl. No.: 83,879

[22] Filed: Aug. 10, 1987

Related U.S. Application Data

[63] Continuation of Ser. No. 867,628, May 27, 1986, abandoned, which is a continuation of Ser. No. 578,500, Feb. 9, 1984, abandoned.

[30] Foreign Application Priority Data

Feb. 10, 1983 [JP] Japan .................................. 58-19689

[51] Int. Cl.⁴ ...................... G03C 1/60; G03C 1/68; G03C 1/49; G03C 1/727
[52] U.S. Cl. ................................... 430/191; 430/175; 430/177; 430/179; 430/190; 430/194; 430/196; 430/270; 430/280; 430/281; 430/343; 430/916; 430/920; 430/925

[58] Field of Search ............... 430/191, 190, 343, 916, 430/920, 925, 175, 177, 179, 194, 196, 270, 280, 281

[56] References Cited

U.S. PATENT DOCUMENTS

| | | | |
|---|---|---|---|
| 3,315,599 | 4/1967 | Lind | 430/49 |
| 3,987,037 | 10/1976 | Bonham et al. | 430/343 |
| 4,160,671 | 7/1979 | Stahlhofer | 430/191 |
| 4,192,677 | 3/1980 | Okazaki et al. | 430/59 |
| 4,212,970 | 7/1980 | Iwasaki | 430/925 |
| 4,232,106 | 11/1980 | Iwasaki et al. | 430/170 |
| 4,279,982 | 7/1981 | Iwasaki et al. | 430/170 |
| 4,448,868 | 3/1984 | Suzuki et al. | 430/58 |
| 4,578,469 | 3/1986 | Deger et al. | 546/66 |
| 4,584,260 | 4/1986 | Iwasaki et al. | 430/920 |

*Primary Examiner*—Charles L. Bowers, Jr.
*Attorney, Agent, or Firm*—Finnegan, Henderson, Farabow, Garrett, & Dunner

[57] ABSTRACT

Light sensitive compositions are disclosed which comprise 2-halomethyl-1,3,4,-oxadiazole compounds having a heterocyclic radical in the fifth position containing at least one element selected from the group consisting of oxygen, nitrogen, sulphur, and selenium directly or through a vinyl radical.

28 Claims, No Drawings

LIGHT-SENSITIVE COMPOSITION

This application is a continuation of application Ser. No. 867,628 filed May 27, 1986, abandoned which is of application Ser. No. 578,500 filed Feb. 9, 1984, abandoned.

FIELD OF THE INVENTION

The present invention relates to a light-sensitive composition containing a 2-halomethyl-1,3,4-oxadiazole compound having a heterocyclic radical in the 5-position of the compound directly or through a vinyl radical.

DESCRIPTION OF THE PRIOR ART

It is known that an organic halide compound is useful as a free radical-producing agent which, when subjected to light, produces a halogen free radical. The halogen free radical acts as a hydrogen-abstracting agent to abstract hydrogen from a hydrogen donor to thereby produce an acid. It is also known that such a nature enables not only to use organic halide compounds as the photopolymerization initiator for photopolymerization reactions or as the catalyst for reactions which need an acid catalyst but also as the print-out agent for printing plate-making materials as in the lithographic process as well as in the letterpress; for the image-forming material in such photographic materials as free radical photographic materials; or for various image-forming materials as a print-out agent.

It is known in Japanese Patent Publication Open to Public Inspection (hereinafter referred to as Japanese Patent O.P.I. Publication) Nos. 74728/1979 and 77742/1980 that as the 2-halomethyl-1,3,4-oxadiazole compound, 2-halomethyl-1,3,4-oxadiazole compound, 2-halomethyl-5-arylvinyl-1,3,4-oxadiazole compounds and 2-halomethyl-5-aryl-1,3,4-oxadiazole compounds are excellent as compared to those conventional free radical-producing agents in that they are capable of producing free radicals to rays over an extensive wavelength range, and, when incorporated into a photosensitive composition, displays a satisfactory compatibility with other elements, and the like.

As a result of our investigation, however, it has now been found that these 5-substituted-2-halomethyl-1,3,4-oxadiazole compounds have the disadvantage that their free radical-producing efficiency is still not sufficient. Such disadvantage in the free radical-producing efficiency, e.g., in chemical reactions, lowers the reaction rate, and, e.g., in image-forming materials which utilize photopolymerization reactions, lowers the image-forming sensitivity. If a large quantity of a conventional 5-substituted-2-halomethyl-1,3,4-oxadiazole compound is used in an attempt to solve this problem, drawbacks occur. For example, when used as the print-out agent in a photosensitive resist-forming composition, although its print-out ability is satisfactory in a way, the increased quantity of the compound deteriorates the resist-forming sensitivity itself, and deteriorates the intrinsic characteristics of the photosensitive resist-forming composition due to the occurrence of stain during the time of printing, and further extremely narrows room for the selection of various component materials due to the lowering of the compatibility of the compound with other elements.

In the status quo it is strongly desirable to develop a novel 2-halomethyl-1,3,4-oxadiazole compound free from the above disadvantages.

SUMMARY OF THE INVENTION

It is therefore an object of the invention to provide a light-sensitive composition having high sensitivity even if it contains an oxadiazole compound.

Another object of the invention is to provide a light-sensitive composition capable of obtaining a sharp and clear printout image, i.e., an exposed visible image, with improved preservability.

A further object of the invention is to provide a light-sensitive composition with excellent developability.

Still a further object of the invention is to provide a light-sensitive composition useful for a highly sensitive positive lithographic printing plate.

As a result of our investigation, we have now found that the above objects of the invention can be accomplished by a light-sensitive composition containing a novel 2-halomethyl-1,3,4-oxadiazole compound.

That is, the 2-halomethyl-1,3,4-oxadiazole compound of the present invention is characterized by having a heterocyclic radical containing at least one element selected from oxygen, nitrogen, sulphur and selenium, directly or through a vinyl radical in the fifth position thereof, the heterocyclic radical being allowed to have a substituent.

DETAILED DESCRIPTION OF THE INVENTION

The preferred in the present invention among the 2-halomethyl-1,3,4-oxadiazole compounds are those having the following Formula [I]:

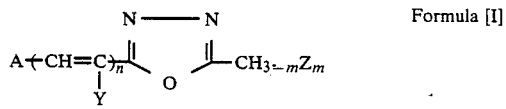

Formula [I]

wherein Z is a halogen atom such as a fluorine atom, chlorine atom or bromine atom, Y is a hydrogen atom, a halogen atom, an alkyl group or an aryl group, A is a heterocyclic radical, m is an integer of from 1 to 3, and n is an integer of 0 or 1.

The preferred alkyl group represented by Y has from 1 to 6 carbon atoms and includes, as typical ones, methyl, ethyl and butyl groups. The aryl group is preferably a phenyl group.

The halogen atom represented by Y is preferably a chlorine atom and a bromine atom.

The preferred heterocyclic radical represented by A is of a ring structure having a great resonance effect containing a hetero element, and includes, as typical ones, a substituted or unsubstituted benzofuryl, dibenzofuryl, thienyl, benzothienyl, dibenzothienyl, indolyl, carbazolyl, selenolyl, benzoselenolyl, dibenzoselenolyl, imidazolyl, benzoimidazolyl, thiazolyl, benzothiazolyl, pyrrolyl and acridyl radicals.

The substituents to the heterocyclic radical include, e.g., as typical ones, an monovalent radical or atom such as an alkyl group, an alkoxy group, a cyano, a nitro, a phenoxy group, a phenyl group, and a halogen atom and a divalent radical such as $-O-CH_2-O-$. Alkyl and alkoxy groups having from 1 to 6 carbon atoms are preferable.

The preferred heterocyclic radicals include, for example, a benzofuryl, dibenzofuryl, benzothienyl, dibenzothienyl, benzoselenolyl, dibenzoselenolyl, and carbazolyl radicals and the like; and the benzofuryl radical is particularly preferred.

The preferred substituents are electron donor type ones such as an alkoxy group and an alkyl group. For example, the preferable positions where the electron donor type groups are substituted are in the 3-, 4- and/or 6-positions when the heterocyclic radical is a benzofuryl radical and the vinyl radical or the oxadiazoyl radical is in the 2-position of the benzofuryl radical, while they are in the 2-, 4- and/or 6-positions when the benzofuryl radical is 3-benzofuryl radical.

Z is preferably a chlorine atom, and m is preferably 3, and n is preferably 1.

The following are the examples of the 2-halomethyl-1,3,4-oxadiazole compounds having a benzofuryl radical in the fifth position thereof, which are preferably usable in the invention:

[Exemplified Compounds]

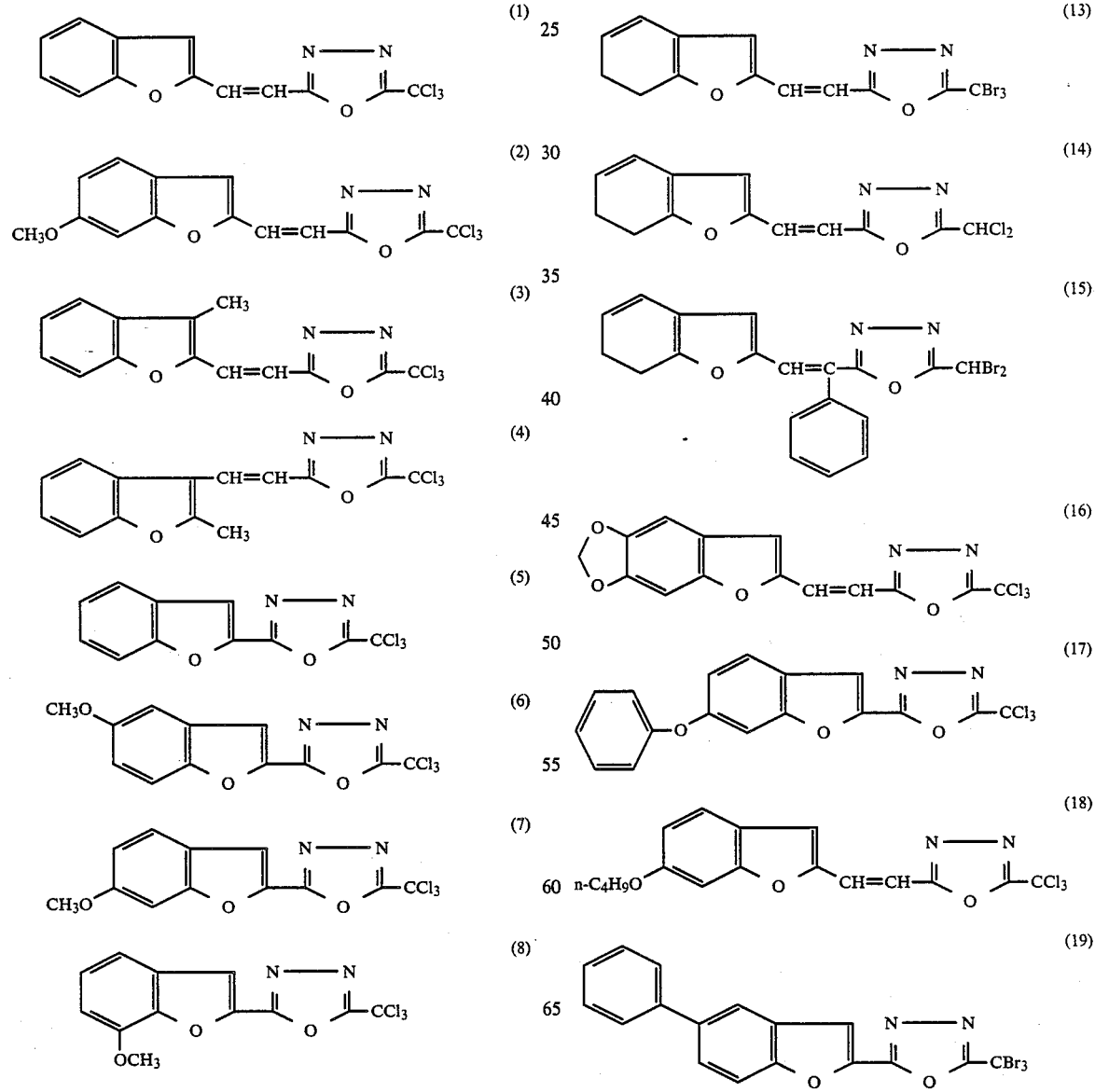

-continued
[Exemplified Compounds]

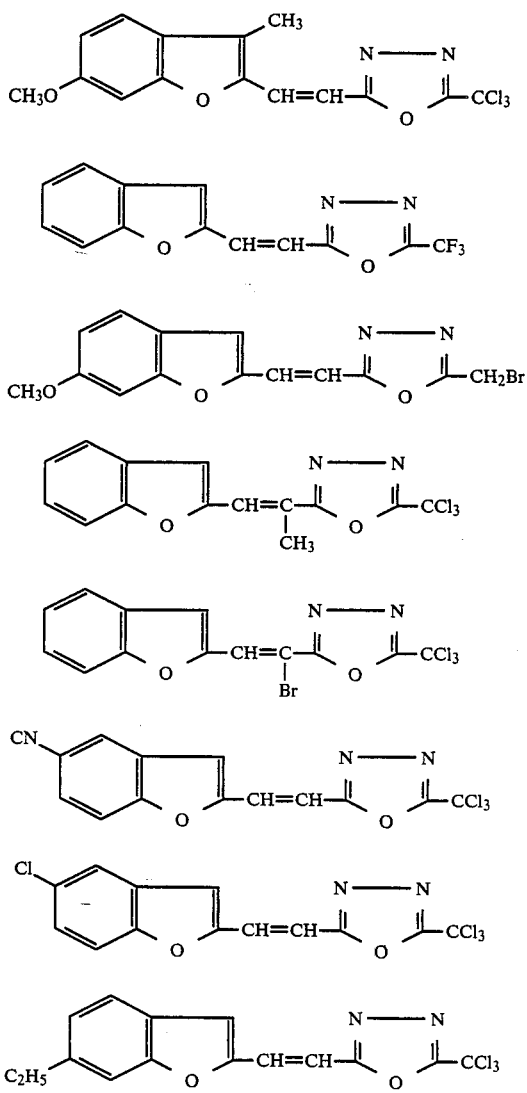

[SYNTHESIS EXAMPLES]

The novel halomethyl-1,3,4-oxadiazole compound having a benzofuran ring in the present invention may be synthesized by a series of, for example, the following reactions: A benzofuran carboxylic acid or β-benzofurylacrylic acid is esterified, and the ester reacts with hydrazine to thereby synthesize a N-hydrzide compound, which is then haloacetylated by use of a haloacetylating agent to thereby synthesize a N,N'-hydrazide compound. The compound is subsequently dehydrated to close its cyclic ring, whereby a 2-halomethyl-1,-3,4-oxadiazole compound which is substituted in the fifth position thereof by a benzofuryl radical or a β-benzofurylvinyl radical can be synthesized. The synthesis of benzofurancarboxylic acids may be carried out in such various ways, including those described in the HETEROCYCLIC COMPOUNDS (published by John Wiley & Sons) vol. 29, pp. 111–140. For example, typical reactions for the synthesis, as described in the "Yukikagobutsu-Gosei-Ho (Methods for the Synthesis of Organic Compounds)" pp. 8 and 32 (published by the Society of Synthetic Organic Chemistry, Japan), may be such that salicylaldehyde and diethyl bromomalonate are heated to react with each other in the presence of potassium carbonate and methyl-ethyl ketone, and hydrolyzed by potassium hydroxide and then acidified, whereby a benzofuran-2-carboxylic acid is synthesized. Benzofuran-2-carboxylic acids whose benzene ring has a substituent may also be synthesized in like manner. β-(benzofuryl)acrylic acids can be easily synthesized in the presence of pyridine by the reaction of malonic acid with a formyl compound which can be synthesized by a method as described in M. Bisagni and Buu-Hoi, J. Chem. Soc. 1955 (3688–3693).

Similar processes may be applied to synthesize a 2-halomothyl-1,3,4-oxadiazole compound having the heterocyclic radical other than a benzofuryl radical in the fifth position thereof.

The following compounds are typically given as examples. First, 2-halomethyl-1,3,4-oxadiazole compounds each having dibenzofuryl radical in the fifth position are exemplified below:

[Exemplified Compounds]

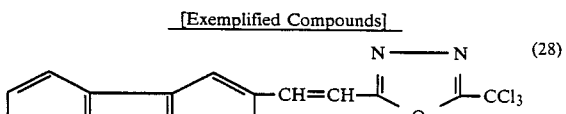

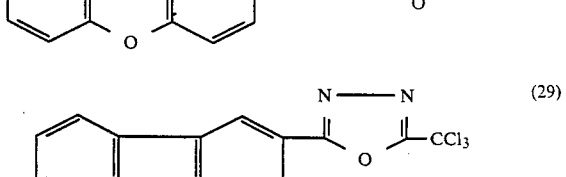

Next, the compound each having a benzothienyl radical or dibenzothienyl radical in the fifth position thereof are exemplified below:

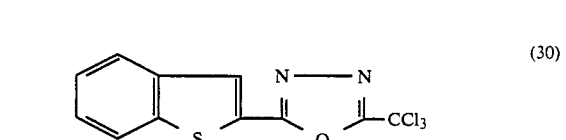

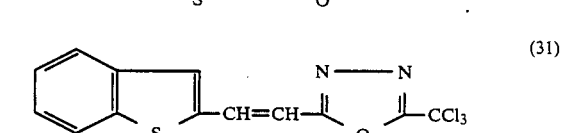

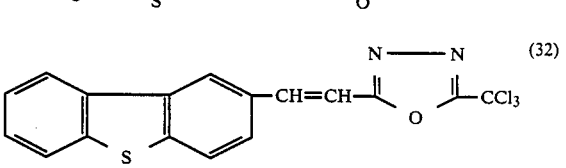

The compounds each having a benzoselenolyl radical or dibenzoselenolyl radical in the fifth position thereof are exemplified below:

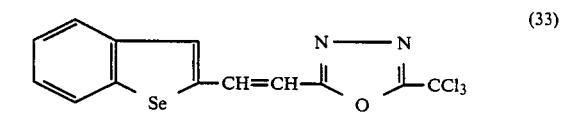

-continued

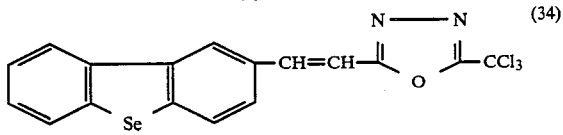 (34)

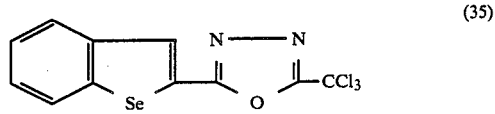 (35)

The compound having a carbazole radical in the fifth position thereof is exemplified below:

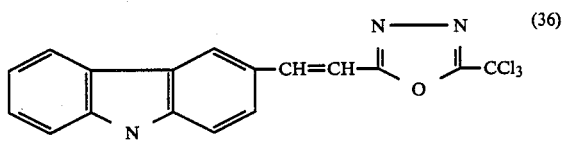 (36)

The compounds each having a heterocyclic radical other than the above in the fifth position thereof are exemplified below:

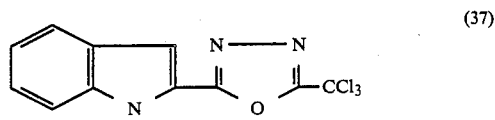 (37)

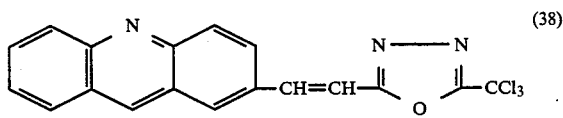 (38)

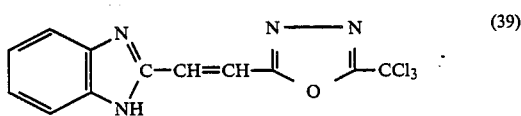 (39)

The above described compounds of the present invention is subjected to the radiation of active rays belonging to the 300-to-500 nm wavelength region to thereby produce a free radical highly efficiently, and further the free radical abstracts hydrogen from a hydrogen donator to thereby produce an acid. Accordingly, the compounds of the present invention are very useful in applications which need the use of free radicals or acids.

The typical application of the light-sensitive compositions of the present invention is the use of it as the print-out agent i.e., exposure visible imaging agent, to be incorporated into the photosensitive resist-forming composition for use in making printing plates, IC circuits, and the like.

Generally speaking, plate-making operations are usually carried out in the yellow light. Obtaining high-contrast and clear images by the exposure alone is very advantageous because it leads to largely improving the efficiency of such work as registering aside from the work of distinguishing between the exposed and unexposed.

The above photosensitive resist-forming compositions which provide print-out images contain as the essential components thereof the compounds of the present invention, and besides, a color-changing agent and a photosensitive resist-forming compound.

As the color-changing agent any material may be used if it can react with the free radical or acid to change the color of the composition. The words "color change" used herein include the meanings that the agent changes from the colorless state to the colored state, and vice versa, and from a certain color to a different color. The preferred color-changing agent is one that reacts with an acid to form a salt to thereby carry out a color change.

For example, Victoria Pure Blue BOH (manufactured by Hodogaya Chemical Co., Ltd.), Oil Blue #603 (Orient Chemical Co., Ltd.), Patent Pure Blue (Sumitomo-Mikuni Chemical Co., Ltd.); triphenylmethane-type, diphenylmethane-type, oxazine-type, xanthene-type, iminonaphthoquinone-type, azomethine-type and anthraquinone-type dyes, represented by crystal violet, brilliant green, ethyl violet, methyl violet, methyl green, erythrosine B, basic fuchsine, malachito green, oil red, m-cresol purple, rhodamine B, auramine, 4-p-diethylaminophenylacetanilide, and the like, are examples of color-changing agents capable of changing from the colored state to the colorless state or from a certain color to a different color.

On the other hand, the color-changing agent capable of changing from the colorless state to the colored state includes primary or secondary arylamine-type dyes such as triphenylamine, diphenylamine, o-chloroaniline, 1,2,3-triphenylguanidine, naphthylamine, diaminophenylmethane, p,p'-bis-dimethylaminophenylamine, 1,2-dianilinoethylene, p,p',p"-tris-dimethylaminotriphenylmethane, p,p'-bis-dimethylaminodiphenylmethylimine, p,p',p"-triamino-o-methyltriphenylmethane, p,p'-bis-dimethylaminodiphenyl-4-anilinonaphthylmethane, and p,p',p"-triaminotriphenylmethane. The preferably dyes are triphenylmethane-type and diphenylmethane-type dyes, and the more preferably usable are triphenylmethane-type dyes, the most preferred dye is Victoria Pure Blue.

The photosensitive resist-forming compounds include those whose nature changes physically and chemically through exposure, such as, e.g., those whose solubility in a developer becomes differentiated, those in which the adherence between the molecules thereof becomes differentiated between before and after the exposure thereof to light, those whose affinities with water and oil, when exposed to light, become differentiated, and the like.

Typical examples of such compounds include, for example, photosensitive diazo compounds, photosensitive azide compounds, ethylenically unsaturated double bonding-having compounds, epoxy compounds that are caused to be polymerized by an acid catalyst, and the like. The photosensitive diazo compounds include those positive-type which, when exposed to light, change to become alkali-soluble, such as o-quinonediazide compounds, and those negative-type whose solubility, when exposed to light, becomes reduced, such as aromatic diazonium salts, and the like.

The o-quinonediazide compounds are compounds having at least one o-quinonediazido radical, particularly o-benzoquinonediazido radical or o-naphthoquinonediazide radical, and include compounds having various structures, such as those compounds as detailed in J. Kosar, the "Light-Sensitive System" (published by John Wiley & Sons, Inc. in 1965) pp. 339 to 353. Particularly the esters or amides produced by the reaction of various hydroxyl compounds or amino compounds with o-naphthoquinonediazidosulfonic acid are suitable.

The preferred hydroxyl compounds include those condensation resins obtained by the condensation of phenols with carbonyl radical-containing compounds, and particularly those resins obtained by the condensation in the presence of an acid catalyst. The above phenols include phenol, resorcinol, cresol, pyrogallol, and the like. The above carbonyl radical-containing compounds include aldehydes such as formaldehyde, benzaldehyde, etc., and ketones such as acetone.

Particularly, phenol-formaldehyde resin, cresol-formaldehyde resin, pyrogallol-acetone resin, and resorcinol-benzaldehyde resin are preferred.

Typical examples of the o-quinonediazide compounds include the ester of benzoquinone-(1,2)-diazidosulfonic acid or naphthoquinone-(1,2)-diazidosulfonic acid with phenol-formaldehyde resin or cresol-formaldehyde resin; the sulfonic acid ester of naphthoquinone-(1,2)-diazidosulfonic acid with pyrogallol-acetone resin as described in U.S. Pat. No. 3,635,709; the condensation product of naphthoquinone-(1,2)-diazido-(2)-5-sulfonic acid with resorcinol-benzaldehyde resin as described in Japanese Patent O.P.I. Publication No. 1044/1981; and the ester compound of naphthoquinone-(1,2)-diazido-(2)-5-sulfonic acid with resorcinol-pyrogallol-acetone copolycondensation product as described in Japanese Patent O.P.I. Publication No. 76346/1980. As other useful o-quinonediazide compounds, the ester of a polyester having, at the terminal thereof, a hydroxyl group with o-naphthoquinone diazidosulfonic acid as described in Japanese Patent O.P.I. Publication No. 117503/1975; the ester of o-naphthoquinonediazidosulfonic acid with a homopolymer of p-hydroxystyrene or with a copolymer of the homopolymer with a monomer copolymerizable therewith as described in Japanese Patent O.P.I. Publication No. 113305/1975; and the like.

The o-quinonediazide compound content of the photosensitive resist-forming composition is preferably from 5 to 80% by weight of the whole solid, and more preferably from 10 to 50% by weight.

As the aromatic diazonium salt, diazo resins represented by the condensation product produced by the condensation reaction of aromatic diazonium salts with formaldehyde may also be used. Those particularly preferred include the salts of the condensation product obtained by the condensation reaction of p-diazodiphenylamine with formaldehyde or with acetaldehyde; for example, inorganic salts of diazo resins such as hexafluorophosphate, tetrafluoroborate, perchlorate, periodate, etc.; the salts of the above condensates with sulfonic acids such as paratoluenesulfonic acid or a salt thereof as described in for example U.S. Pat. No. 3,300,309; diazo resin organic salts, the reaction products produced by the above condensates with phenolic hydroxyl radical-containing compounds such as 2,4-dihydroxybenzophenone; and the like.

As the photosensitive azide compound, those aromatic azide compounds wherein an azide radical is linked directly or through a carbonyl radical or a sulfonyl radical to an aromatic cyclic ring are preferably used. These compounds include, for example, polyazidostyrenes, polyvinyl-p-azidobenzoates, polyvinyl-p-azidobenzals as being described in U.S. Pat. No. 3,096,311; reaction products produced by the reaction of azidoarylsulfonyl chloride with unsaturated hydrocarbon-type polymers as described in Japanese Patent Examined Publication No. 9613/1970; polymers having sulfonylazide radical or carbonylazide radical as described in Japanese Patent Examined Publication Nos. 21067/1968, 229/1969, 22954/1969 and 24915/1970; and the like.

As the ethylenically unsaturated double bonding-having compound there are those effecting photo-double-bonding reactions and those effecting photopolymerization reactions.

As examples of the former, those containing photopolymers as the principal component thereof, such as the esters, polyamides, polycarbonates each containing

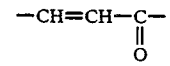

as the main or side polymer chain, may also be suitably usable; for example, such photosensitive polyesters obtained by the condensation of phenylenediethyl acrylate with hydrogenated bisphenol A and triethylene glycol as described in Japanese Patent O.P.I. Publication No. 40415/1980; and such photosensitive polyesters derived from (2-propelidene) malonic acid compounds such as cinnamylidenemalonic acid, etc., and bifunctional glycols; and the like.

As examples of the latter there are those acrylic acid or methacrylic acid ester derivatives including such polyol acrylic acid or methacrylic acid esters as, e.g., diethylene glycol (meth)acrylate, triethylene glycol (meth)acrylate, etc., as described in Japanese Patent Examined Publication Nos. 5093/1960 and 14719/1960.

Among the above-described photosensitive resist-forming compounds, the oxadiazole compounds of the present invention are particularly effectively usable for positive-type lithographic printing plates which use particularly o-naphtoquinonediazide compounds.

The photosensitive resist-forming compound may, if necessary, be used in combination with a binder. The preferred binder for use with the o-quinoneazide compound is an alkali-soluble resin. The preferred alkali-soluble resins are those which can be obtained by combining phenols with ketones or with aldehydes in the presence of an acid catalyst. The phenols usable herein include, for example, phenol, cresol and p-substituted phenols, and the like. The aldehydes include, e.g., acetaldehyde, formaldehyde, and the like, of which the formaldehyde is preferred. Of the ketones, acetone is preferred.

The preferred alkali-soluble resins include, e.g., phenol-formaldehyde resins; cresol-formaldehyde resins, those phenol-cresol-formaldehyde copolycondensate resins as described in Japanese Patent O.P.I. Publication No. 57841/1980; those copolycondensate resins produced from p-substituted phenols with phenol or from cresol with formaldehyde as described in Japanese Patent O.P.I. Publication No. 127553/1980; resorcinol-benzaldehyde resins; condensates produced from polyhydrated phenols with benzaldehyde, such as pyrogallol-benzaldehyde resin; copolycondensates produced from polyhydrated phenols with acetone, such as pyrogallol-resorcinol-acetone resin; and xylenol-formaldehyde resin.

The alkali-soluble resin content of the photosensitive composition is preferably from 30 to 90% by weight to the whole solid, and more preferably from 50 to 85% by weight.

As the binder to be used with the diazonium salt, various macromolecular compounds can be used, which include those monomers having aromatic hydroxyl radicals as described in Japanese Patent O.P.I. Publication No. 98613/1979, such as, copolymers of N-(4-hydroxyphenyl)acrylamide, N-(4-hydroxyphenyl)methacrylamide, o-, m- or p-hydroxystyrene, o-, m- or p-hydroxyphenyl methacrylate, etc., with other monomers; those polymers containing as the main repeating units the hydroxyethyl acrylate unit or the hydroxyethyl methacrylate unit as described in U.S. Pat. No. 4,123,276; natural resin such as shellac, rosin, etc.; polyvinyl alcohols; those liner polyurethane resins as described in U.S. Pat. No. 3,660,097; phthalated polyvinyl alcohol resins; epoxy resins produced by the condensation reaction of bisphenol A with epichlorohydrin; cellulose compounds such as cellulose acetate, cellulose acetate-phthalate, etc.; and the like.

The photosensitive resist-forming composition, in addition to the above-described materials, may, if necessary, also effectively contain various low-molecular compounds such as, e.g., phthalates, triphenyl-phosphates, maleates, such preservation-stabilization agents as, e.g., oxalic acid, phosphoric acid, etc.; surfactants as the coating-improving agent such as fluorosurfactant, and nonionic surfactants such as ethyl cellulose polyalkylene-ethers; such sensitizers as acid anhydrides, etc.; such compounds having a halogen for keeping the after-development contrast and acid-dissociating when exposed to light as, e.g., o-naphthoquinonediazido-4-sulfonyl halides; and the like.

The photosensitive resist-forming composition of the present invention is prepared by coating the above-described components on an appropriate support in generally known manner. To 100 parts by weight of the photosensitive resist-forming composition, from 0.001 to 80 parts by weight of the novel oxadiazole compound of the present invention (most preferably from 0.01 to 40 parts by weight); from 0.1 to 50 parts by weight of the color-changing agent (most preferably from 1 to 10 parts by weight); up to 5000 parts by weight of the binder (most preferably up to 1000 parts by weight); up to 1000 parts by weight of the plasticizer (most preferably up to 500 parts by weight); and up to 50 parts by weight of the sensitizer (most preferably up to 20 parts by weight) are effectively used.

The photosensitive resist-forming composition is dissolved into a solvent and the solution is coated and dried on an appropriate support suitable for uses. The usable solvent includes ethylene glycol monomethyl ether, ethylene glycol monoethyl ether, ethylene glycol monomethyl ether acetate, ethylene dichloride, cyclohexanone, methylcellosolve acetate, methyl-ethyl ketone, dimethylformamide, and the like. As the support, for example, when used for the lithographic process, sand-blasted aluminum plates, sand-blasted and anodic oxidation-treated aluminum plates, zinc plates, chrome-plated steel plates, chromic acid-treated copper plates, plastic film treated to be hydrophilic, paper, and the like, may be used, and when used as the support for photomask film or other image-forming materials, polyethylene terephthalate, cellulose triacetate, those films, glass plates and copper plates each having various metals deposited thereon by vacuum evaporation, and the like, may be effectively used.

The appropriate coating amount for the solid components is from 0.1 to 10.0 g/m$^2$, and in the case of the photosensitive lithographic printing plate, preferably from 0.2 to 8.0 g/m$^2$, and most preferably from 0.5 to 4.0 g/m$^2$.

The halomethyl-1,3,4-oxadiazole compound having a heterocyclic radical in the fifth position relating to the present invention is excellent, e.g., in the free radical-producing efficiency, i.e., the acid productivity, as compared to those conventionally known 2-halomethyl-1,3,4-oxadiazole compounds, so that the amount of the former, when used as photo-Lewis acid-producing agent, can be small in various uses, and there is no need to worry about its compatibility with and its effect upon other components when adding thereto, and its stability with lapse of time is satisfactory.

The following are synthesis examples of the compound of the present invention and examples of the present invention, but the present invention is not limited thereto.

SYNTHESIS EXAMPLES

Synthesis Example-1 (Synthesis of Exemplified Compound (1))

171.8 g of $\beta$-(2-benzofuryl)acrylic acid, synthesized in the manner as described in J. Chinese Chem. Soc. sev. II 8, pp. 374–379, and 101.5 g of triethylamine were added to 550 ml of acetone, to the mixture were added dropwise 75.9 g of chloroacetonitrile, and the mixture was refluxed by heating over a period of five hours. After the reaction, 400 ml of water were added to cool the reaction system, and the deposited crystals were filtered by a suction filter and then washed. The obtained crystals were recrystallized from acetone to thereby obtain 187 g of $\beta$-(2-benzofuryl)acrylic acid cyanomethyl ester having a melting point between 119° C. and 121° C.

187 g of the $\beta$-(2-benzofuryl)acrylic acid cyanomethyl ester were added to 2 liters of methanol, and to the mixture, with stirring, were added 76.8 g of hydrazine hydrate, and then the resulting mixture was refluxed by heating for 30 minutes. After the reaction, 2 liters of water were added to cool the reaction product, and the deposited crystals were filtered by a suction filter, then washed, and then recrystallized from methanol, thereby obtaining 150 g of $\beta$-(2-benzofuryl)acrylic acid hydrazide having a melting point between 173° C. and 174° C.

150 g of the $\beta$-(2-benzofuryl)acrylic acid hydrazide were added to 600 ml of acetonitrile, and when to the mixture, with stirring, were added 196 g of hexachloroacetone, an exothermic reaction took place. Then the reaction system was allowed to stand for about 30 minutes at about 60° C., and the reaction liquid was cooled, whereby 170 g of N-$\beta$-(2-benzofuryl)-acryloyl-N'-trichloroacetyl-hydrazide having a melting point between 226° C. and 229° C. were obtained.

124 g of the N-$\beta$-(2-benzofuryl)acryloyl-N'-trichloroacetyl-hydrazide were added to 300 ml of phosphorus oxychloride. After a one-hour reflux by heating, the reaction system was cooled and then poured in a small flow into 2 liters of iced water to thereby decompose the excess of the phosphorus oxychloride. The resulting precipitate was filtered by a suction filter, then washed and then recrystallized from an acetone-water mixture at room temperature, whereby 97.4 of a yellow prism-crystalline 2-trichloromethyl-5-[$\beta$-(2'-benzofuryl)vinyl]-1,3,4-oxadiazole (m.p. 133°–135° C.) were obtained.

Elemental Analysis: $C_{13}H_7N_2O_2Cl_3$

|  | C | H | N |
|---|---|---|---|
| Calculated: | 47.47 | 2.14 | 8.50 |
| Found: | 47.63 | 2.01 | 8.28 |

Ultraviolet Absorption Spectrum
λmax: 342 nm : $3.77 \times 10^4$ (methanol solution)

Synthesis Example-2 (Synthesis of Exemplified Compound (5))

81 g of benzofuran-2-carboxylic acid and 50 g of triethylamine were added to 550 ml of ethyl acetate, and to the mixture were further added 40 g of chloroacetonitrile, and the mixture was refluxed by heating for 3 hours. The deposited crystals were removed and the solvent was distilled off, and the obtained crystals were recrystallized from methanol to thereby obtain 85 g of benzofuran-2-carboxylic acid cyanomethyl ester having a melting point between 74° C. and 76° C.

35 g of the benzofuran-2-carboxylic acid hydrazide were added to 140 ml of acetonitrile, and to this were further added 53 g of hexachloroacetone. The resulting mixture was refluxed by heating for 2 hours. After the reaction to this were added 200 ml of water. The deposited crystals were filtered, thereby obtaining 57 g of N-(2-benzofuryl)formyl-N'-trichloroacetyl-hydrozide having a melting point between 146° C. and 150° C.

45 g of the N-(2-benzofuryl)formyl-N'-trichloroacetyl-hydrazide were added to 100 ml of phosphorus oxychloride. After a 2-hour reflux by heating, the reaction system was cooled and then poured in a small flow into 1 liter of iced water to decompose the excess of the phosphorus oxychloride, whereby crystals were precipitated. The precipitate was filtered by a suction filter, and to this was added the same quantity of water to thereby recrystallize the product, whereby 35 g of a white prism-crystalline 2-trichloromethyl-5-(2'-benzofuryl)-1,3,4-oxadiazole (m.p. 147°–149° C.) were obtained.

Elemental Analysis $C_{11}H_5N_2O_2Cl_3$

|  | C | H | N |
|---|---|---|---|
| Calculated: | 43.53 | 1.66 | 9.23 |
| Found: | 43.78 | 1.46 | 9.01 |

Ultraviolet Absorption Spectrum
λmax: 302 nm : $2.67 \times 10^4$ (methanol solution)

Synthesis Example-3 (Synthesis Exemplified Compound (2)):

11 g of 2-hydroxy-4-methoxybenzaldehyde, 20.3 g of ethyl bromomalonate, 12.3 g of potassium carbonate, and 51 ml of methyl-ethyl ketone were put into a three-necked flask, and refluxed to hold the reaction thereof for 6 hours. After that to this was added a methanol solution of potassium hydroxide, and at a point of time of completion of the hydrolysis reaction, the hydrolyzed product was put into an aqueous hydro chloric acid solution, and then filtered, whereby a 6-methoxybenzofuran-2-carboxylic acid having a melting point between 208° C. and 211° C. was obtained.

9.6 g of the filtrated carboxylic acid were dissolved into a mixture of 4.5 g of chloroacetontrile, 5 g of triethylamine and 80 ml of ethyl acetate, and refluxed for 2 hours to effect the reaction thereof. After the reaction the reaction product was filtered, washed, then dried, and then recrystallized from acetone, whereby a 6-methoxybenzofuran-2-carboxylic acid ester having a melting point between 122° C. and 124° C. was obtained.

9.6 of the produced ester were dissolved into a mixture of 116 ml of methanol and 3.6 g of 80% hydrazine hydrate. After a one-hour reaction by refluxing, to the reaction mixture was added to water to deposit crystals, which were then filtrated and recrystallized from methanol, whereby a 6-methoxbenzofuran-2-carboxylic acid hydrazide having a melting point between 127° C. and 128° C. was obtained.

7.6 g of the hydrazide compound were dissolved into 40 ml of pyridine, and to the solution were added dropwise 8.1 g of benzenesulfonyl chloride. After making sure of completion of the reaction for 2 hours at room temperature, the produced crystals were filtered, and then recrystallized from an acetone-water mixture, whereby a 6methoxybenzofuran-2-(β-benzenesulfonyl-hydrazine)-carboxylic acid hydrate having a melting point between 207° C. and 211° C. was obtained.

10 g of the thus produced hydrazide were dissolved into 80 ml of ethylene glycol and, after the nitrogen substitution, its temperature was raised to between 150° C. and 160° C., and to this were added 80 g of sodium carbonate. After an ether extraction, the product was washed and then dried to thereby distill off the solvent.

Next, 3.6 g of the aldehyde and 2.3 g of malonic acid were dispersed into 5 ml of pyridine, and then the mixture was caused to react by heating over an oil bath, and to this was added hydrochloric acid to thereby deposit crystals, which were subsequently recrystallized from an acetone-water mixture, thereby obtaining a 6-methoxybenzofuryl-2-carboxylic acid having a melting point between 208° C. and 210° C.

A 2-trichloromethyl-5-{β-[2'-(6''-methoxy)benzofuryl]-vinyl}-1,3,4-oxadiazole having a melting point between 120° C. and 122° C. was obtained by synthesizing in the same manner as in Synthesis Example-1 by using the above 6-methoxybenzofuryl-2-carboxylic acid in place of the β-(2-benzofuryl)acrylic acid used in Synthesis Example-1.

Elemental Analysis $C_{14}H_9N_2O_3Cl_3$

|  | C | H | N |
|---|---|---|---|
| Calculated: | 48.94 | 2.64 | 8.15 |
| Found: | 49.20 | 2.51 | 8.30 |

Ultraviolet Absorption Spectrum
λmax: 370 nm ε: $3.53 \times 10^4$ (methanol solution)

Synthesis Example-4:

Exemplified Compounds (3), (4), (6), (7), (8), (9), (10), (11) and (12) were synthesized by using the corresponding benzofuran carboxylic acids or benzofurylacrylic acids, respectively, in place of the benzofuran-2-carboxylic acid of Synthesis Example-2. The results of their melting points, elemental analyses and ultraviolet absorption spectra are given in the following table.

| Exemplified compound | Melting point | Elemental analysis | | | | UV absorption spectrum | |
|---|---|---|---|---|---|---|---|
| | | | C | H | N | λmax | ε |
| (3) | 173–174 | Calculated | 48.94 | 2.64 | 8.15 | 350 | $3.99 \times 10^4$ |
| | | Found | 48.80 | 2.67 | 8.26 | | |
| (4) | 123–125 | Calculated | 48.94 | 2.64 | 8.15 | 325 | $2.33 \times 10^4$ |
| | | Found | 49.13 | 2.59 | 7.99 | | |
| (6) | 142–144 | Calculated | 43.21 | 2.12 | 8.40 | 285 | $1.68 \times 10^4$ |
| | | Found | 42.98 | 2.17 | 8.57 | | |
| (7) | 144–146 | Calculated | 43.21 | 2.12 | 8.40 | 328 | $2.91 \times 10^4$ |
| | | Found | 43.46 | 2.10 | 8.36 | | |
| (8) | 122–127 | Calculated | 43.21 | 2.12 | 8.40 | 295 | $2.84 \times 10^4$ |
| | | Found | 43.39 | 2.14 | 8.19 | | |
| (9) | 176–178 | Calculated | 42.95 | 2.50 | 7.71 | 333 | $2.34 \times 10^4$ |
| | | Found | 43.10 | 2.46 | 7.59 | | |
| (10) | 176–178 | Calculated | 37.91 | 1.16 | 12.06 | 271 | $2.95 \times 10^4$ |
| | | Found | 37.70 | 1.19 | 11.91 | | |
| (11) | 94–98 | Calculated | 45.38 | 2.22 | 8.82 | 275 | $1.94 \times 10^4$ |
| | | Found | 45.57 | 2.20 | 8.60 | | |
| (12) | 178–180 | Calculated | 44.92 | 2.61 | 8.06 | 329 | $2.85 \times 10^4$ |
| | | Found | 44.80 | 2.65 | 7.90 | | |

Synthesis Example-5 [Synthesis of Exemplified Compound (28)]

Formylated dibenzofuran may be synthesized by the application of the well-known Vilsmeyer's reaction.

Phosphorus oxychloride of 35 g was dropped into 18.2 g of DMF by cooling with ice, and about 30 minutes later 34.8 g of dibenzofuran was added therein in nitrogen flow, and thus, the reaction was continued for 12 hours long at 50° to 80° C.

Next, the resulted reactant was dissolved with stirring in 260 ml of ice water and was then hydrolyzed upon heating. After the reaction, water was separated, and 31 g of formylated dibenzofuran was obtained.

Thereafter, β-(dibenzofuryl)acrylic acid is synthesized in the process described in M. Bisagni, Buu-Hoi, J. chem. Soc., 1955, No. 3688, pp. 36–93. The synthesization is readily performed by reacting a formyl substance on malonic acid in the presence of pyridine.

Exemplified compounds up to (28) may be synthesized in the process similar to that used in Synthesis example-1.

Exemplified compounds (13) through (39) may also be synthesized in the processes similar to those used in Synthesis Examples-5 and -6.

Example-1

The following photosensitive liquid was coated over a 0.24 mm-thick aluminum plate whose surface was sand-blasted and subjected to an anodic oxidation treatment and then dried for 4 minutes at 100° C., whereby a lithographic printing plate was obtained.

| | |
|---|---|
| Product produced by the esterification reaction of naphthoquinone-(1,2)-diazido-5-sulfonyl chloride with resorcinol-benzaldehyde resin (esterification degree 50%, the compound described in Japanese Patent O.P.I. Publication No. 1044/1981) | 3.0 g |
| Cresol-novolak resin | 12.0 g |
| Exemplified compound (1) | 0.09 g |
| Glutaric anhydride | 0.13 g |
| Victoria Pure Blue BOH (Hodogaya Chemical Co., Ltd.) | 0.12 g |
| Crystal Violet | 0.03 g |
| Methyl cellosolve | 100.0 g |

The weight of the coated layer after drying was 2.4 g/m². The lithographic printing plate with which a halftone original film was brought into close contact was exposed for 140 seconds to a 2 KW metal halide lamp light with its radiation illuminace of 8.0 mW/Cm². Immediately after the exposure, an image clearly perceivable in detail was obtained. The lithographic printing plate was subsequently developed for 45 seconds at 25° C. in a 7-fold diluted developer of the following composition to thereby obtain a lithographic printing plate. On the other hand, in order to examine the tendency of stain appearance, the lithographic printing plate was processed in an exhausted developer, and applied to a printing press. The obtained results are as shown in Table 1, wherein the results of the print-out image are shown with the difference in the density through an orange filter between the exposed and unexposed areas along with the appearance by the eye.

| Developer Composition: | |
|---|---|
| Sodium silicate (SiO₂ 28–30%, Na₂O 9–10%) | 134 g |
| Sodium hydroxide | 12 g |
| Water | 890 ml |

Next, the exposure time was severally changed so as to obtain the effective sensitivity, i.e., the exposure time in which 49.1% of the halftone original film may be reproduced on a plate to 39.1%. The results are exhibited in Table 1.

Comparative Example-1

A comparative sample was prepared and tested in the same manner as in Example-1 with the exception that a 2-trichloromethyl-5-(p-methoxystyryl)-1,3,4-oxadiazole compound as described in Japanese Patent Examined Publication No. 6096/1982 was used in the same quantity as that of and in place of the Exemplified Compound (1) in the photosensitive liquid used in Example-1.

Comparative Example-2

A comparative sample was prepared and tested in the same manner as in Example-1 with the exception that the using quantity of the 2-trichloromethyl-5-(p-methoxystyryl)-1,3,4-oxadiazole compound that was used in Comparative Example-1 was increased to 0.15 g.

Comparatic Example-3

A comparative sample was prepared and tested in the same manner as in Example-1 with the exception that a 2-trichloromethyl-5-(β-naphthylvinyl)-1,3,4-oxadiazole compound as described in Japanese Patent Examined Publication No. 6096/1982 was used in the same quantity as that of and in place of the Exemplified Compound (1) in the photosensitive liquid used in Example-1.

[Compound]

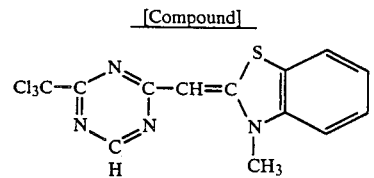

TABLE 1

| | Exposed print-out visible image quality | | | | Plate-making characteristics | | |
|---|---|---|---|---|---|---|---|
| | Appearance by eye | Optical density | | | Number of steps (clear) | Stain when processed in exhausted developer* | effective sensitivity** |
| | | Unexposed area | Exposed area | ΔD | | | |
| Example-1 | ◉ | 0.86 | 0.68 | 0.18 | 5 | None | 140 |
| Comparative example-1 | △ | 0.85 | 0.76 | 0.09 | 5 | None | 145 |
| Comparative example-2 | ◉ | 0.85 | 0.68 | 0.17 | 3.5 | Present | 198 |
| Comparative example-3 | △ | 0.85 | 0.79 | 0.06 | 5 | None | 166 |
| Example-2 | ◉ | 0.86 | 0.73 | 0.13 | 5 | None | 134 |
| Comparative example-4 | △ | 0.85 | 0.81 | 0.04 | 5 | None | 143 |
| Comparative example-5 | △ | 0.85 | 0.80 | 0.05 | 5 | None | 166 |
| Comparative example-6 | ○ | 0.86 | 0.75 | 0.11 | 4 | None | 181 |

Note:
* The developer which has developed overall exposed PS plates for $3m^2$/liter.
** the exposure time in which 49.1% of the halftone original film may be reproduced on a plate to 39.1%

Example-2

A sample was prepared and tested in the same manner as in Example-1 with the exception that Exemplified Compound (5) was used in the same quantity as that of and in place of the Exemplified Compound (1) in the photosensitive liquid used in Example-1.

Comparative Example-4

A comparative sample was prepared and tested in the same manner as in Example-1 with the exception that a 2-trichloromethyl-5-phenyl-1,3,4-oxadiazole compound as described in Japanese Patent O.P.I. Publication No. 77742/1980 was used in the same quantity as that of and in place of the Exemplified Compound (1) in the photosensitive liquid used in Example-1.

Comparative Example-5

A comparative sample was prepared and tested in the same manner as in Example-1 with the exception that a 2-trichlormethyl-5-β-naphthyl-1,3,4-oxadiazole compound as described in Japanese Patent O.P.I. Publication No. 77742/1980 was used in the same quantity as that of and in place of the Exemplified Compound (1) in the photosensitive liquid used in Example-1.

Comparative Example-6

A comparative sample was prepared and tested in the same manner as in Example-1 with the exception that the following compound was added in the same quantity as that of and in place of the Exemplified Compound (1) in the photosensitive liquid used in Example-1.

As apparent from the results shown in Table 1, the printing plate samples of Examples-1 and -2 containing the oxadiazole compound of the present invention enable to obtain much clearer images in the same quantity of the compound as that of conventional oxadiazole compounds than those of Comparative Examples-1 and -3 through -5 containing the conventional compounds. In order to obtain print-out images having the same density as that of the samples of the present invention by using conventional oxadiazole compounds, the conventional compound must be added in a larger quantity (Comparative Example-2), thus resulting in unsatisfactory development with stain appearing on the printing plate.

The results also show that the compounds each having a heterocyclic radical relating to the invention display excellent exposure visible imaging characteristics and other lithographic characteristics as compared with the compounds containing conventional and well-known phenyl radicals as given in Comparative Example 4 and naphthyl radicals having highly effective conjugation as given in Comparative Example 5.

On the other hand, the results also show that the compounds relating to the invention are superior to conventionally known trihaloalkyl compounds as given in Comparison Example 6 each having heterocyclic radical in a triazine ring position in the exposure visible imaging characteristics, the lithographic characteristics and, in particular, the step-sensitivity and the effective sensitivity. Example-3

In place of Exemplified Compound (1), Exemplified Compound (28) was added in the same quantity into the light-sensitive liquid used in Example-1, and the resulted was evaluated similarly. The similar results were obtained.

Example-4

On a similar aluminum plate to the one used in Example-1, the following photosensitive liquid was coated and dried, whereby a lithographic printing plate sample was obtained.

| | | |
|---|---|---|
| | p-toluenesulfonate of the condensate produced from p-diazodiphenylamine with paraformaldehyde | 0.8 g |
| | Acrylonitrile-methacrylic acid-methyl methacrylate-p-hydroxymethacrylamide copolymer | 10.0 g |
| | Exemplified Compound (2) | 0.08 g |
| | Methyl violet | 0.08 g |
| | Methyl cellosolve | 130.0 g |

The thus obtained lithographic printing plate was exposed to light in the same manner as in Example-1. Immediately after that, a print-out image perceivable in detail was obtained.

Example-5

On a similar aluminum plate to the one used in Example-1 the following photosensitive liquid was coated and dried, whereby a lithographic printing plate sample was obtained.

| | | |
|---|---|---|
| | Photosensitive polyester, the condensate produced from phenylenediethyl acrylate, hydrogenated bisphenol A and ethylene glycol (the compound described in Japanese Patent O.P.I. Publication No. 40415/1980) | 4.0 g |
| | Copper phthalocyanine | 5.0 g |
| | Exemplified Compound (2) | 0.09 g |
| | Crystal violet | 1.0 g |
| | Cyclohexanone | 100.0 g |

The obtained lithographic printing plate was exposed to light in the same manner as in Example-1. Immediately after that, a print-out image perceivable in detail was obtained.

What is claimed is:

1. A light-sensitive composition comprising
   (a) a 2-halomethyl-1,3,4-oxadiazole compound of Formula I

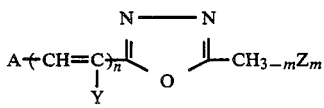

wherein, Z is a fluorine atom, a chlorine atom or a bromine atom; Y is a hydrogen atom, a halogen atom, an alkyl group or an aryl group, wherein A is a substituted or unsubstituted benzofuryl-radical, m is an integer of from 1 to 3, and n is an integer of 0 or 1,
   (b) a coloring agent, and
   (c) a light sensitive resist forming compound,
   each of said 2-halomethyl-1,3,4-oxidiazole compound, said coloring agent and said light sensitive resist forming compound being present in an amount effective to provide a photosensitive resist forming composition capable of providing print-out images.

2. The light-sensitive composition as claimed in claim 1, wherein the alkyl group represented by Y is an alkyl group having one to six carbon atoms.

3. The light-sensitive composition as claimed in claim 1, wherein the halogen atom represented by Y is a chlorine atom or bromine atom.

4. The light-sensitive composition as claimed in claim 1, wherein Y is a hydrogen atom.

5. The light-sensitive composition as claimed in claim 1, wherein m is 3.

6. The light-sensitive composition according to claim 1, wherein A is a benzofuryl-radical which may be independently substituted by one or more substituents selected from the group consisting of an alkyl group, an alkoxy group, a cyano group, a nitro group, a phenoxy group, a phenyl group, a halogen atom and a —O—CH$_2$—O— group.

7. The light-sensitive composition according to claim 1, wherein A is an unsubstituted benzofuryl radical.

8. The light-sensitive composition according to claim 1, wherein said light-sensitive resist-forming compound has an o-benzoquinone diazide radical or an o-naphthoquinone diazide radical.

9. A light-sensitive composition according to claim 1, wherein said coloring agent is a triphenyl methane dye.

10. A light-sensitive composition according to claim 6, wherein said light-sensitive resist-forming compound has an o-benzoquinone diazide radical or an o-naphthoquinone diazide radical.

11. A light-sensitive composition according to claim 7, wherein said light-sensitive resist-forming compound has an o-benzoquinone diazide radical or an o-naphthoquinone diazide radical.

12. A light sensitive composition comprising:
    (a) a free radical producing agent, said free radical producing agent being a 2-halomethyl-1,3,4-oxadiazole compound of the following Formula:

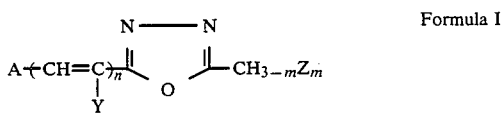

wherein, Z is a fluorine atom, a chlorine atom or a bromine atom; Y is a hydrogen atom, a halogen atom, an alkyl group or an aryl group, A is a heterocyclic radical containing at least one element selected from the group consisting of oxygen, nitrogen, sulphur and silenium, m is an interger of from 1 to 3, and n is an integer of 0 or 1,
   (b) a coloring agent, and
   (c) a light sensitive resist forming compound,
   each of said 2-halomethyl-1,3,4-oxidiazole compound, said coloring agent and said light sensitive resist forming compound being present in an amount effective to provide a photosensitive resist forming composition capable of providing print-out images.

13. The light-sensitive composition as claimed in claim 12, wherein said heterocyclic radical is a substituted or unsubstituted benzofuryl-, dibenzofuryl-, thienyl-, benzothienyl-, dibenzothienyl-, indolyl-, carbazolyl-, selenolyl-, benzoselenolyl-, dibenzoselenolyl-, imidazolyl-, benzoimidazolyl-, thiazolyl-, benzothiazolyl-, pyrrolyl-, or acridyl- radical.

14. The light-sensitive composition as claimed in claim 13, wherein the alkyl group represented by Y is an alkyl group having one to six carbon atoms.

15. The light-sensitive composition as claimed in claim 13, wherein the halogen atom represented by Y is a chlorine atom or bromine atom.

16. A light-sensitive composition according to claim 13, wherein A is a substituted or unsubstituted radical selected from the group consisting of a benzofuryl-, dibenzofuryl-, benzothienyl-, dibenzothienyl, benzoselenolyl-, dibenzoselenolyl- and carbazolyl-.

17. The light-sensitive composition according to claim 13, wherein said light-sensitive resist-forming compound has an o-benzoquinone diazide radical or an o-naphthoquinone diazide radical.

18. A light-sensitive composition according to claim 13, wherein said coloring agent is a triphenyl methane dye.

19. The light-sensitive composition as claimed in claim 13, wherein the heterocyclic radical represented by A is a benzofuryl radical.

20. The light-sensitive composition as claimed in claim 19 wherein Y is a hydrogen atom.

21. The light-sensitive composition as claimed in claim 19, wherein the heterocyclic radical represented by A is a 2-benzofuryl radical.

22. The light-sensitive composition as claimed in claim 13, wherein Y is a hydrogen atom.

23. The light-sensitive composition as claimed in claim 22, wherein m is 3.

24. The light-sensitive composition as claimed in claim 12, wherein said coloring agent is a triphenyl methane dye.

25. The light-sensitive composition as claimed in claim 12, wherein said light-sensitive resist-forming compound has an o-benzoquinone diazide radical or an o-naphthoquinone diazide radical.

26. The light-sensitive composition as claimed in claim 25, wherein the contents of said o-quinone diazide compound are 10 to 50% by weight to the total solids of the light-sensitive composition.

27. The light-sensitive composition as claimed in claim 12, wherein said composition contains, to 100 parts by weight of the light-sensitive resist-forming compound, 0.01 to 40 parts by weight of the 2-halomethyl-1,3,4-oxadiazole compound and 1 to 10 parts by weight of the coloring agent.

28. The light-sensitive composition as claimed in claim 12, wherein the heterocyclic radical is a 2-benzofuryl radical.

* * * * *